(12) United States Patent
Falkner et al.

(10) Patent No.: US 7,025,970 B2
(45) Date of Patent: Apr. 11, 2006

(54) MODIFIED POXVIRUSES, INCLUDING MODIFIED SMALLPOX VIRUS VACCINE BASED ON RECOMBINANT DRUG-SENSITIVE VACCINIA VIRUS, AND NEW SELECTION METHODS

(75) Inventors: Falko-Guenter Falkner, Orth/Donau (AT); Georg Holzer, Vienna (AT); Sogue Coulibaly, Vienna (AT); Josef Mayrhofer, Vienna (AT)

(73) Assignees: Baxter International Inc., Deerfield, IL (US); Baxter Heathcare S.A., Zurich (CH)

( * ) Notice: Subject to any disclaimer, the term of this patent is extended or adjusted under 35 U.S.C. 154(b) by 377 days.

(21) Appl. No.: 10/388,234

(22) Filed: Mar. 14, 2003

(65) Prior Publication Data

US 2003/0228330 A1 Dec. 11, 2003

Related U.S. Application Data

(60) Provisional application No. 60/364,117, filed on Mar. 15, 2002.

(51) Int. Cl.
*A61K 39/285* (2006.01)
*A61K 39/42* (2006.01)

(52) U.S. Cl. .............................. 424/232.1; 424/199.1; 424/93.2; 424/159.1

(58) Field of Classification Search ............. 424/199.1, 424/232.1, 93.2, 159.1; 435/235.1, 320.1, 435/471, 239
See application file for complete search history.

(56) References Cited

U.S. PATENT DOCUMENTS

| 4,603,112 A | * | 7/1986 | Paoletti et al. ........... 435/235.1 |
| 5,856,153 A | * | 1/1999 | Tiraby et al. ................ 435/455 |
| 2003/0031681 A1 | * | 2/2003 | McCart et al. ........... 424/186.1 |

OTHER PUBLICATIONS

Mackett et al PNAS 79:7415-7419, 1982.*
Metzger et al Journal of Virology 8423-8427, 1994.*
McCart et al Gene Therapy 7:1217-1223, 2000.*
Kesson et al Clinical Infectious Diseases 25:911-4, 1997.*
Smith et al (PNAS 93:7955-79760, 1995).*
Chakrabarti et al (PNAS 93:9810-9815, 1996).*

* cited by examiner

Primary Examiner—Mary E. Mosher
(74) Attorney, Agent, or Firm—Heller, Ehrman; John P. Isacson (57) ABSTRACT

The present invention provides recombinant poxviruses, such as vaccinia virus, that contain an integrated exogenous sequence, such as a foreign gene, encoding a prodrug converting polypeptide that can convert a prodrug to a drug that prevents virus replication or is otherwise toxic to the virus. The recombinant poxviruses can be suitable for use as vaccines. The invention also provides, among other things, methods of inhibiting virus replication, methods of vaccination and methods of treating vaccinated subjects showing signs or otherwise at risk for of vaccination-induced disease.

14 Claims, 5 Drawing Sheets

A  tk/tmk  vtk-suci2

B  VV-tk  D4R  VV-wt

C  tdk/tmk  vsuci2-L

MODIFIED POXVIRUSES, INCLUDING MODIFIED SMALLPOX VIRUS VACCINE BASED ON RECOMBINANT DRUG-SENSITIVE VACCINIA VIRUS, AND NEW SELECTION METHODS

This application claims priority to U.S. provisional application Ser. No. 60/364,117, filed Mar. 15, 2002, the entirety of which is hereby incorporated by reference.

BACKGROUND OF INVENTION

Vaccinia virus (VV), long considered the archetypal poxvirus, has long been a tool in biomedical research and vaccination purposes, and several recombinant poxvirus constructs are undergoing scientific review for various vaccine purposes. Vaccinia is considered representative of the other poxviruses.

Recombinant poxviruses have been generated by in vivo homologous recombination using a broad number of selection markers. See, for example, Mackett et al., *Proc. Nat'l Acad. Sci. USA* 79: 7415–19 (1982). Another approach for producing recombinant poxviruses is known as "direct molecular cloning." See U.S. Pat. Nos. 6,103,244 and 5,445,953, both of which are incorporated by reference. Falkner et al., *Ency. Life Sci.* 1–4 (2001) and Moss, *Proc. Nat'l Acad. Sci. USA* 93: 11341–48 (1996) provide overviews of poxvirus technology.

Frequently-used procedures for generating recombinant poxviruses employ (i) thymidine kinase (tk)-negative selection by insertional inactivation of the endogenous vaccinia tk-gene, (ii) color screening using the *E. coli* β-galactosidase gene and (iii) dominant positive selection using the *E. coli* hypoxanthine-guanine phosphoribosyl-transferase (gpt) marker. These approaches allow for appropriately stringent selection for standard constructions with replicating parental poxviruses.

One major in vivo application for poxviruses is the use of vaccinia as a smallpox vaccine. This vaccine has led to the elimination of smallpox as a naturally-occurring disease. World events, such as the increasing threat of bioterrorism, have raised the specter of smallpox being employed as a biological weapon. See Dove, *Nature Medicine* 8: 197 (2002). Accordingly, large scale smallpox vaccination of populations is under active consideration.

Past vaccination programs have shown that the conventional smallpox vaccine is not without risk. See Lane et al., *New Eng. J. Med.* 281:1201–1208 (1969); Lane et al., *J. Infect. Dis.* 122:303–309 (1970). There are several adverse events, including diseases, associated with the conventional smallpox vaccine. These events are described below.

Postvaccinial Encephalitis

Postvaccinial encephalitis, although occurring infrequently, is one of the most serious adverse events associated with conventional smallpox vaccines. This adverse event is manifested by severe demyelinating encephalitis. The case-fatality rate is approximately 30 to 35%. Neurological sequelae are frequent with this adverse event, and include cognitive deficits and paralysis.

Post-vaccinal encephalitis typically is a complication of primary vaccination. The maximum risk of post-vaccinal encephalitis in adults following primary vaccination appears to be in the range of 3 to 9 affected patients per million vaccinated adults.

Progressive Vaccinia (vaccinia necrosum)

Progressive vaccinia is a serious adverse event usually seen only in immunosuppressed persons, such as those with hereditary or acquired immunodeficiency disorder, or undergoing treatment with immunosuppressive medications.

Progressive vaccinia is characterized by failure of the primary cutaneous lesion to heal. Symptoms include progressive enlargement and spreading, necrosis of the lesion, and appearance of other lesions, which in turn progress. The case-fatality rate is high (40 to 85%), with death generally occurring 2 to 5 months after vaccination.

The incidence of progressive vaccinia has been low (1 to 3 affected patients per million vaccinated subjected). This complication was more frequent in adults than children, and reflected the presence of tumors of the reticuloendothelial system (lymphoma or leukemia). HIV/AIDS, however, represents a risk factor for progressive vaccinia that was not seen during the era of wide-spread smallpox vaccination.

Eczema vaccinatum

Eczema vaccinatum is a serious adverse event that occurs in individuals with active or quiescent eczema, and is characterized by the appearance of cutaneous lesions in skin. Large areas of skin usually become involved, and there are severe systemic effects, such as fever and lymphadenitis. The case fatality rate is less than 10%.

Generalized Vaccinia.

Generalized vaccinia can occur in immunocompetent persons. Affected persons develop a generalized rash following vaccination. This illness is characterized by multiple skin lesions resembling the local reaction at the vaccination site, and can be accompanied by fever and chills. The highest incidence of this complication occurs in children who are less than 1 year of age.

Ocular Complications

Accidental infection of the eye of a contact results in infection of the eyelid, conjunctiva and, in some cases, the cornea. Corneal involvement (keratitis) is the most serious complication, occurring principally in persons undergoing primary vaccination. Keratitis is relatively infrequent, occurring in less than 10% of cases with ocular infection. The incidence of ocular vaccinia was approximately 10 affected patients per million vaccinated subjects.

The diagnosis of these adverse events is recognizable by the healthcare practitioner. Past treatment approaches have included the use of vaccinia immune globulin (VIG), but the overall effectiveness of these interventions with diseases resulting from conventional smallpox vaccines is uncertain.

Current Practices

Classical vaccinia strains are being increasingly replaced by highly attenuated and/or nonreplicating viruses for safety reasons. These replacement viruses are restricted to a relatively narrow host range. The nonreplicating vectors MVA (modified vaccinia Ankara) or NYVAC (New York vaccinia virus, derived from the Copenhagen strain), for instance, are propagated in primary chicken embryo fibroblasts. Although nonreplicating vaccinia vectors are safe, they often do not induce sufficient amounts of neutralizing antibodies when used as a single vaccine.

Other approaches for increasing safety include the use of poxviruses having disrupted or inactivated essential regions, typically through the insertion of foreign DNA into the essential regions. These viruses are permissive for growth only when complemented, such as through the use of engineered complementing cell lines. See, for example, U.S.

Pat. No. 5,766,882 (which is incorporated by reference); Holzer et al., *J. Virol.* 71:4997–5002 (1997).

The vaccinia tk-gene, mentioned above for use in creating recombinant poxviruses, has exhibited a high tendency for spontaneous mutations. These mutations render the tk selection approach leaky (susceptible to the generation of tk-negative viruses without a foreign DNA insert). Thus, more stringent negative selectable markers are needed to permit better screening approaches and facilitate identification of essential poxviral genes. A clear identification of essential genes still depends on conditionally lethal mutations that can be mapped to a respective locus. Deletions enforced by a previously inserted dominant negative marker, should discriminate between essential and non-essential genes, even when no temperature sensitive mutants exist for that locus.

Vaccinia virus, both native and recombinant strains, can be inhibited by a variety of compounds. See De Clerc, *Clin. Microbiol. Rev.* 14:382–397 (2001). However, no drug is currently approved for treatment of generalized vaccinia infection, and only few drugs would be acceptable for treatment of humans according to their respective spectrum of side-effects. Drugs known to inhibit vaccinia efficiently, such as bromodeoxyuridine (BrdU), are not selective and inhibit also growth of the host cells. The thiosemicarbazones, which are potent inhibitors of vaccinia and smallpox virus, seem to be toxic to cells and are not approved medications for any indication. The most promising anti-vaccinia drug currently appears to be cidofovir, an antiviral approved for cytomegalovirus (CMV) infection. Cidofovir has been shown to reduce mortality in immunocompetent mice when challenged with cowpox virus; although it only delayed but did not prevent death of SCID mice. Cidofovir is administered by the intravenous route. Cidofovir treatment, however, requires hospitalization of patients because nephrotoxicity has to be prevented by infusions of normal saline before and after drug infusions. In addition, monitoring of kidney function is required, thereby making cidofovir treatment an expensive and sophisticated treatment option.

Other antiviral drugs, such as Azidothymidine (AZT), have been shown to inhibit replication of human immunodeficiency virus (HIV) do not normally inhibit vaccinia virus.

There are anti-viral alternatives to AZT. The control of HIV spread in a cell culture or an organism by other approaches has been described. Smith et al., *Proc. Nat'l Acad. Sci. USA* 93: 7955–7960 (1996) disclosed an effective vaccine approach for human HIV-1 employing a live-attenuated virus, wherein the virus is modified to express the herpes simplex virus (HSV) tk gene. The spread of HIV-1 in tissue culture is shown to be controllable by the addition of the drug gancyclovir (GCV). Chakrabarti et al., *Proc. Nat'l Acad. Sci. USA* 93: 9810–9815 (1996) described a candidate live attenuated vaccine for AIDS comprising a genetically modified HIV-1 virus comprising a HSV-tk gene as a controllable conditional lethal marker. Because the HSV-tk gene confers on the virus a preference of the prodrugs GCV and Acyclovir (ACV) over its normal substrate thymidine or guanine, the addition of the prodrugs permits control of the virus load in infected individuals whom have received the vaccine. However, the approach has risks due to the possible generation of escape mutants caused by the high mutation rate of HIV.

Recombinant vaccinia has been engineered for uses other than in vaccines. Recombinant vaccinia that confers drug sensitivity to tumor cells can be used as a cancer gene therapy approach. See Higginbotham et al. (12th Poxvirus Meeting, USA 1998). In addition, Metzger et al. *J. Virol.* 68: 8423–8427 (1994) disclosed a recombinant vaccinia comprising the coding sequence for cytomegalovirus (CMV) UL97 gene, which makes vaccinia susceptible to GCV. In this report, vaccinia is used as a tool to characterize a herpes virus tk gene encoded by ORF UL97. McChart et al. *Gene Therapy* 7:1217–1223 (2000) describes replicating viruses for cancer gene therapy, in particular a recombinant vaccinia expressing the cytosine deaminase gene, which converts the prodrug 5-fluorocytosine (5-FC) to 5-fluorouracil (5-FU). 5-FU has an anti-tumor effect and also an anti-viral effect.

BRIEF SUMMARY OF THE INVENTION

In view of the limitations of the prior art approaches, there is still a need for a novel replicating smallpox vaccine that has a similar immunogenicity and efficacy profile as the replicating standard vaccine and is administered the same way as a standard replicating smallpox vaccine, but can be controlled by well-tolerated compounds to provide a treatment option in case of adverse effects.

It is therefore an object of the invention to provide a modified poxvirus, such as one that can be used as a smallpox vaccine.

In accomplishing this and other objects, there are provided, in accordance with one aspect of the invention recombinant poxviruses, such as vaccinia, wherein the poxviruses have integrated into their viral genomes one or more exogenous sequences encoding polypeptides under transcriptional control of a poxvirus regulatory regions, wherein said polypeptide confers susceptibility of the poxvirus to an antiviral compound. Preferably, the recombinant poxviruses are suitable for use as vaccines. The exogenous sequences can encode prodrug converting polypeptides that can convert a prodrug to a drug that inhibits poxviral replication. Exogenous sequences can be mutant or native in terms of their source, and include foreign genes, complete and incomplete open reading frames and synthetic sequences encoding active proteins, polypeptides or fragments thereof. The vaccine can be in a pharmaceutically acceptable carrier, preferably comprising $\geq 10^8$ pfu/ml of vaccinia virus. The vaccines can be administered by all standard smallpox vaccination routes, including scarification.

In accordance with another aspect of the invention, there are provided smallpox vaccines comprising recombinant vaccinia virus having integrated into the viral genome an exogenous sequence encoding a prodrug converting polypeptide under transcriptional control of a poxvirus regulatory region, wherein said prodrug converting polypeptide can convert a prodrug into a drug that inhibits viral replication. The vaccinia virus can be a smallpox vaccine strain selected from the group of strains consisting of Lister/Elstree, New York City Board of Health, Temple of Heaven, and LC16m0. The exogenous sequence can be integrated into a non-essential region of the viral genome, such as an intergenic region or a non-essential gene.

In accordance with a still further aspect of the invention, there are provided methods, in particular in vitro methods, of generating and selecting recombinant poxvirus containing genes of interest using prodrugs for negative selection.

The prodrug converting polypeptide can be a thymidine kinase from herpes simplex virus or cytomegalovirus, such as those encoded by CMV UL97 or herpes ORF UL97. As an alternative, the prodrug converting polypeptide can be a cytosine deaminase gene. The prodrug converting polypeptide can be a fusion protein, such as *E.coli* thymidine kinase/thymidylate kinase (tk/tmk). The prodrug can be a nucleoside analog. Exemplary prodrugs include 3' azido-2', 3'-dideoxythymidine (AZT), gancyclovir (GCV), acyclovir (ACV) and 5-FC. Prodrugs can be administered prior to, concurrent with, or after vaccination in doses effective to treat any adverse event associated with the poxvirus, and will typically result in the reduction of virus titer through the inhibition of replication. In the most typical situation, the prodrug is administered after clinical signs of an adverse event, such as a disease, become apparent.

In accordance with another aspect of the present invention, there are provided methods to treat vaccinated subjects showing signs, clinical or otherwise, of vaccination-induced disease after vaccination with a smallpox virus vaccine having integrated into its viral genome an exogenous sequence encoding a prodrug converting polypeptide under transcriptional control of a poxvirus regulatory region, wherein the method comprises the step of administering to the vaccinated subject a prodrug for a time sufficient to at least reduce the titer of the smallpox virus vaccine, wherein the prodrug is converted by the prodrug converting polypeptide to a drug that inhibits viral replication, wherein the therapy can be monitored by determination of viral load of the vaccinated subject. The treatment can further comprise administering an anti-vaccinia immune globulin to the vaccinated subject. The vaccinia virus can be a smallpox vaccine strain selected from the group of strains consisting of Lister/Elstree, New York City Board of Health, Temple of Heaven, and LC16m0. The exogenous sequence can be integrated into a non-essential region of the viral genome, such as an intergenic region. The prodrug can be given orally, intravenously, topically, or by other known routes.

The prodrug converting polypeptide can be a thymidine kinase from herpes simplex virus or cytomegalovirus, such as those encoded by CMV UL97 or herpes ORF UL97. As an alternative, the prodrug converting polypeptide can be a cytosine deaminase gene. The prodrug converting polypeptide can be a fusion protein, such as E.coli thymidine kinase/thymidylate kinase (tk/tmk). The prodrug can be a nucleoside analog. Exemplary prodrugs include 3' azido-2', 3'-dideoxythymidine (AZT), gancyclovir (GCV), acyclovir (ACV) and 5-FC.

In accordance with still another aspect of the invention, there are provided recombinant vaccinia viruses, which can be used as a vaccine, having integrated into the viral genome an exogenous sequence encoding a prodrug converting polypeptide under transcriptional control of a poxvirus regulatory region, wherein said prodrug converting polypeptide can convert a prodrug into a drug that inhibits viral replication. The vaccinia virus can be a smallpox vaccine strain selected from the group of strains consisting of Lister/Elstree, New York City Board of Health, Temple of Heaven, and LC16m0. The exogenous sequence can be integrated into a non-essential region of the viral genome, such as an intergenic region. Preferably, the vaccinia virus has a reversion rate of less than $1:10^4$ in cell culture.

In accordance with yet another aspect of the invention, there are provided methods of inhibiting replication of a recombinant vaccinia virus having integrated into its viral genome an exogenous sequence encoding a prodrug converting polypeptide under transcriptional control of a poxvirus regulatory region, wherein the method comprises infecting an organism with the recombinant vaccinia virus and treating said organism with a prodrug selected from the group consisting of 3' azido-2',3'-dideoxythymidine (AZT), gancyclovir (GCV), acyclovir (ACV) and 5-FC. The organism can be a microorganism or a large organism, such as a mammal. These methods find application in a variety of contexts, including treatment of adverse events resulting from vaccination.

In accordance with a further aspect of the invention, there are provided methods of vaccinating subjects against smallpox, wherein the method comprises administering to the subject a recombinant vaccinia virus having integrated into its viral genome an exogenous sequence encoding a prodrug converting polypeptide under transcriptional control of a poxvirus regulatory region, wherein said prodrug converting polypeptide can convert a prodrug into a drug that inhibits vaccinia virus replication. The vaccinia virus can be a smallpox vaccine strain selected from the group of strains consisting of Lister/Elstree, New York City Board of Health, Temple of Heaven, and LC16m0. The exogenous sequence can be integrated into a non-essential region of the viral genome, such as an intergenic region. If needed, the prodrug can be given orally, intravenously or topically.

In accordance with a still further aspect of the invention, there are provided methods of generating and selecting recombinant poxviruses containing genes of interest using prodrugs for negative selection. An exemplary method includes transforming host cells containing a parental poxvirus that contains a region that includes an exogenous sequence encoding a prodrug converting polypeptide flanked by poxvirus sequences with an insertion polynucleotide, such as a plasmid, that comprises the exogenous sequence of interest that is flanked by poxvirus sequences that are homologous to the sequences in the region of the parental poxvirus, wherein homologous recombination can occur between the parental poxvirus and the insertion polynucleotide such that the exogenous sequence of interest is inserted into the parental poxvirus and the exogenous sequence encoding the prodrug converting polypeptide is excised therefrom so as to form the recombinant poxvirus that expresses the exogenous sequence of interest; propagating the transformed host cells; contacting the host cells with the prodrug, wherein host cells infected with the parental virus have the prodrug converted to the drug to inhibit viral replication of the parental virus; and harvesting the recombinant poxvirus that expresses the exogenous sequence of interest.

These and other aspects of the present invention will become apparent to the skilled artisan in view of the description contained herein.

BRIEF DESCRIPTION OF THE FIGURES

FIG. 1 depicts a schematic representation of viruses. The virus vtk-suci2 has the tk/tmk marker integrated in the vaccinia tk-locus (A). The wild-type virus (VV-wt) is shown in (B). In the virus vsuci2-L (C), the suicide gene is inserted in the intergenic region of open reading frames (ORFs) D4R and D5R.

FIG. 2 depicts the inhibition of the drug-sensitive virus vsuzi2-L by AZT. Tenfold dilutions of a virus stock were used to infect CV-1 cells. After virus adsorption, medium containing 0.75 mg/ml AZT is added to the cells and incubation is continued for three days. Monolayers were stained with crystal violet. In the presence of AZT, the virus is strongly inhibited (upper row). In the absence of the drug the virus grows normally. At the highest dose (10,000 pfu/well) the monolayer is completely lysed, while with AZT, only minute lesions were seen.

FIG. 3 contains photographs of the animal model for generalized vaccinia disease. Balb/c SCID mice develop generalized vaccinia when challenged subcutaneously with the Lister strain within 3–4 weeks after inoculation with $10^8$ pfu per animal. Typical lesions are seen on tail, paws and mouth region.

FIG. 4 depicts a schematic representation of the selection procedure. The drug-sensitive parental virus carries the suicide gene tk/tmk preferably in an intergenic region flanked by vaccinia sequences (fl1, fl2). The insertion plasmid has the same flanking regions including a transgene and a positive selection marker (TG/+m). The first plaque purification is done by positive selection (for instance gpt/lacZ screening), resulting in recombinants still contaminated with parental virus. The second step is a negative AZT-selection, actively removing contaminating parental virus.

FIG. 5 depicts a schematic representation of an approach for selecting defective viruses. The parental replicating AZT-sensitive virus has a tk/tmk marker gene inserted in the intergenic region of ORFs D4R and D5R. Homologous recombination with an insertion plasmid carrying the transgene (TG) (a type of exogenous sequence) of interest and a gpt/lacZ (gptz) marker flanked by sequences of the D3R and the D5R ORF results, using the positive/negative selection steps in the rapid generation of defective viruses having the essential gene D4R deleted. If the marker gene is flanked by direct repeats, the virus thereby obtained is marker-free.

DETAILED DESCRIPTION OF THE INVENTION

The present invention provides, among other things, a new and improved smallpox vaccine based on a drug-sensitive recombinant vaccinia virus, which can be derived from a standard smallpox vaccine strain or other strains, including attenuated strains. The novel vaccine can be administered the same way as a standard smallpox vaccine and has a similar immunogenicity and efficacy profile as the standard vaccine. However, by virtue of the integrated exogenous sequence encoding a prodrug converting polypeptide under the control of a poxvirus regulatory region, the virus can be inhibited, if needed, by relatively well-tolerated standard antiviral drugs. The exogenous sequence can be integrated most anywhere in the poxvirus genome, but preferably in a non-essential region. The vaccinia thymidine kinase gene is one such region. Moreover, because poxviruses have practically no overlapping genes, there are hundreds of intergenic regions that are non-essential and thus can be used as regions for insertion. See U.S. Pat. No. 5,670,367 (which is incorporated by reference); Spehner et al, *J. Virol.*, 64: 527: 33 (1990); Esposito et al., *Virol.* 165: 313–16 (1988); Moss et al., *J. Virol.* 40: 387–95 (1981); Weir et al., *Proc. Nat'l Acad. Sci. USA* 79: 1210–14 (1982); Archard et al., *J. Gen. Virol.* 45: 51–63 (1979); Moyer et al., *Virol.* 102: 119–32 (1980); Dumbell and Archard, *Nature* 286: 29–32 (1980).

A vaccine comprising a drug-sensitive recombinant vaccinia virus permits treatment of complications arising from vaccinia infections by using approved and immediately available prodrugs. The term "treat" in its various grammatical forms in relation to the present invention refers to preventing, curing, reversing, attenuating, alleviating, minimizing, suppressing or halting the deleterious effects of an adverse event, disease state, disease progression, disease causative agent (e.g., virus) or other abnormal condition. The term "regulatory region" denotes any sequence or sequences that control or affect the transcription of DNA into RNA or the translation of RNA into a protein and are functional in a given context (e.g., in the vaccinia virus). Exemplary of such regulatory regions are promoters, ribosome binding sites, and translation start sites, and these regions can have the same sequence as naturally occurring regions or can be altered through synthetic mutagenesis techniques. Many poxvirus promoters are available to the skilled person. See U.S. Pat. No. 5,670,367; Wyatt et al., *Vaccine* 14: 1451–58 (1996); Davison et al., *J. Mol. Biol.* 210: 749–69 (1989); Davison et al., *J. Mol. Biol.* 210: 771–84 (1989); Fleming et al., *Virol.* 187:464–71 (1992); Boursnell et al., *J. Gen. Virol.* 71: 621–28 (1990); Boursnell et al., *Virol.* 178: 297–300 (1990); Esposito et al., *Virol.* 165: 313–316 (1988); van der Leek et al., *Vet. Rec.* 134: 13–18 (1994); Patel et al., *Proc. Nat'l Acad. Sci. USA* 85: 9431–35 (1988); Kumar et al., *Arch. Virol.* 112: 139–48 (1990); Pearson et al., *Virol.* 180: 561–66 (1991).

The prodrug converting polypeptide for use according to the invention can be a thymidine kinase from herpes simplex virus or cytomegalovirus, such as those encoded by CMV UL97 or herpes ORF UL97. As an alternative, the prodrug converting polypeptide can be a cytosine deaminase gene. The prodrug converting polypeptide can be a fusion protein, such as *E.coli* thymidine kinase/thymidylate kinase (tk/tmk). Tk and tmk genes can be derived from a variety of viruses and living sources. The prodrug can be a nucleoside analog. Exemplary prodrugs include 3' azido-2',3'-dideoxythymidine (AZT), gancyclovir (GCV), acyclovir (ACV) and 5-FC. Other prodrugs include ddi, ddc, d4T, 3TC, and abacavir.

Side effects of the prodrugs themselves well-studied and are tolerable, at least for short term treatment. The prodrugs can be administered, for example, orally as a tablet one or more times a day or as a syrup for children, as known by the medical practitioner and/or pharmacist. Other administration approaches available to the healthcare practitioner are appropriate.

Dosing of the prodrugs can be done in accordance with the efficacy profiles of these compounds, and by known administration routes. The dosages and treatment periods should be selected to be effective to treat the adverse event by a resulting reduction in the titer of the poxvirus. Overall dose levels on the order of about 0.1 mg to about 10,000 mg of the prodrugs are useful in the treatment of the above conditions, with preferred levels being about 1 mg to about 5,000 mg. The specific dose level, and thus the therapeutically-effective amount, for any particular patient can vary depending upon a variety of factors, including the activity of the specific prodrug employed and its bioavailability at the site of drug action; the age, body weight, general health, immune state, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models also are helpful. The considerations for determining the proper dose levels are available to the skilled person employing recognized techniques.

In the case of nucleoside analogs that also are employed for treatment of HIV, dosing, administration, efficacy, tolerance and side effects of these compounds are known. In the context of HIV, these analogs may need to be administered of the course of a lifetime due to the mutational capabilities of HIV. In the context of the present invention, however, the prodrugs need not be administered nearly that long. The need for continued prodrug administration can be ascertained by determining poxviral load, such as through the use of PCR, or it can be done on a symptomatic basis by evaluating the remission of the disease. Typically, the prodrugs will be given for less than 1 month, usually 2 to 4 weeks. In the case of AZT, the dosing will typically be 300 to 600 mg per day for 2 to 4 weeks. Gancyclovir can be administered at 5 to 10 mg/kg/day, and acyclovir can be administered at 500–4000 mg/day. 5-FC can be administered at 100 mg/kg/day. Treatment periods for any prodrug can be readily determined and monitored by PCR and/or clinical evaluation in view of the known properties of these compounds.

In general, pharmaceutically acceptable carriers for use according to the invention include aqueous solutions, non-toxic excipients, including salts, preservatives, buffers and the like, as described in UNITED STATES PHARMACOPEIA AND NATIONAL FORMULARY (USP 24-NF 19); REMINGTON'S PHARMACEUTICAL SCIENCES; HANDBOOK ON PHARMACEUTICAL EXCIPIENTS (2d ed., Wade and Weller eds., 1994), the contents of all are hereby incorporated by reference. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the binding composition are adjusted according to routine skills in the art. See GOODMAN AND GILMAN'S THE PHARMACOLOGICAL BASIS FOR THERAPEUTICS (9th ed.), the contents of which are hereby incorporated by reference.

Treatment of vaccinated subjects is typically initiated when signs, clinical or otherwise, of vaccination-induced disease become apparent, which is known by the healthcare practitioner. Treatment of vaccinated subjects also can be initiated for subjects at risk for vaccination-induced disease, such as immunocompromised or immunosuppressed patients, which is within the judgment of the healthcare practitioner. Immunocompromised and immunosuppressed patients include patients infected with HIV, suffering from hereditary defects or engaged in immunosuppressive therapies, such as taking anti-rejection medications.

Due to the rate of adverse events with standard smallpox vaccines, the invention significantly improves the safety of smallpox vaccination without compromising vaccine efficacy. The invention also includes the use of anti-vaccinia immune globulin (VIG) in combination with the prodrug.

The virus can be produced with protein-free cell culture technology, such as the use of Vero cells grown in protein-free media (which lacks serum proteins, among other things). See, for example, U.S. Pat. No. 6,146,873, which is hereby incorporated by reference.

The present invention also provides for a new selection method of recombinant vaccinia based on a drug-sensitive vaccinia virus comprising the coding sequence for a prodrug converting polypeptide as described in the present invention. In contrast to the conventional vaccinia thymidine kinase (tk) selection that is performed in tk-negative cell lines, prodrug selection can be performed in tk-positive cell lines. This allows the rapid generation of vaccinia recombinants and for defective recombinants where classical tk selection cannot be performed. The drug-sensitive virus displays a surprisingly low mutation rate resulting in an at least 1000-fold lower occurrence of escape mutants, a prerequisite to successfully suppress virus growth in vaccinated subjects.

One exemplary suicide gene for use according to the invention is the *E. coli* tk/tmk fusion gene, although tk and tmk genes from other species and mutant forms of tk and tmk genes can be employed in accordance with the teachings of the invention. One suitable gene is a thymidine kinase/thymidylate kinase (tk/tmk) fusion (InvivoGen, Inc., USA) and encodes an enzyme that efficiently converts the prodrug 3'-azido-2',3'-dideoxythymidine (AZT) into its toxic triphosphate derivative AZT-TP, which stops DNA chain elongation in cells where the gene is active. Wild-type vaccinia virus replicating in a host cell cannot be inhibited by AZT, implying that the endogenous vaccinia tk-gene and also the host cell enzymes do not use the prodrug efficiently. See also Reynes et al., *J. Bacteriol.* 178:2804–2812 (1996). Integration of the tk/tmk suicide gene into vaccinia virus, that normally is not inhibited by AZT, allows the establishment of a powerful dominant negative selection procedure for recombinant viruses. This prodrug-converting enzyme is used as an example in the construction of recombinant vaccinia being used in a smallpox virus vaccine.

Figure 1:
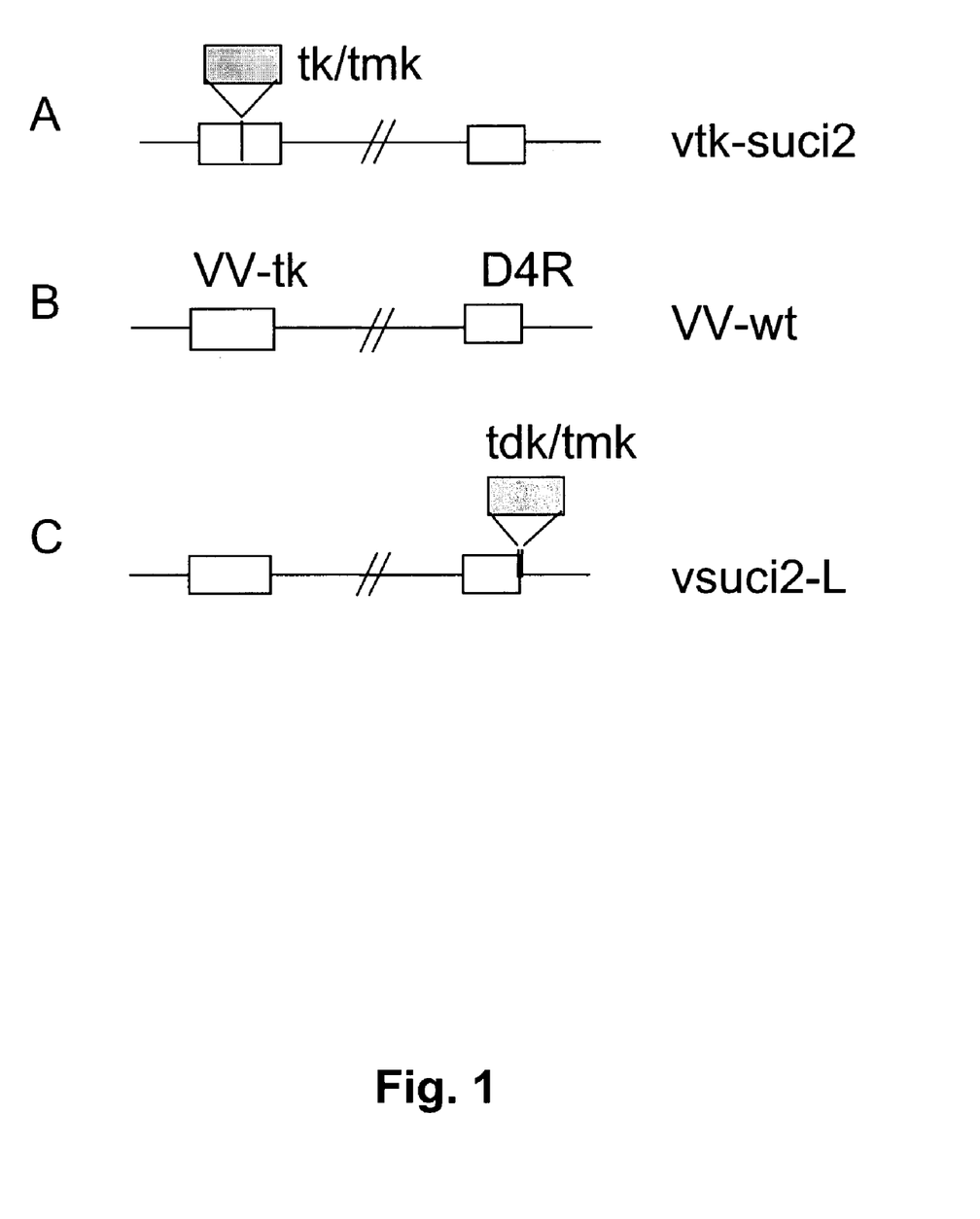
Figure 2:
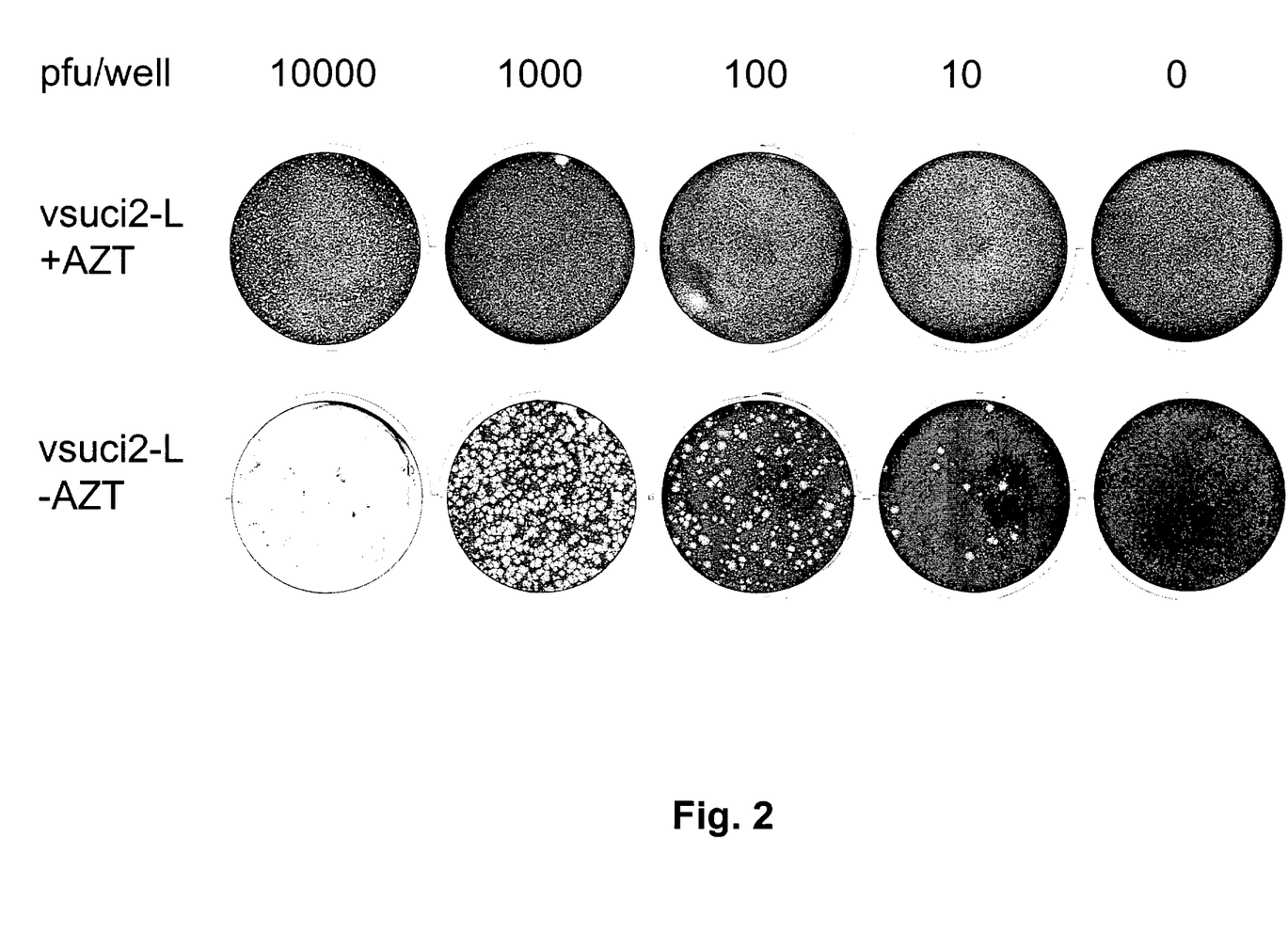

As further proof of concept that the *E. coli* tk/tmk marker when integrated into vaccinia allows inhibition of viral replication, recombinant viruses were constructed containing the tmk/tdk gene under control of the vaccinia P7.5 early/late promoter (FIGS. 2A, C). The insertion plasmids ptk-D4-suci and pDD4.4-suci2, used in the recombination experiments, direct the P7.5 tk/tmk gene cassette into the viral tk-locus and into the D4R/D5R intergenic region, respectively. The viruses permit to conduct inhibition experiments in vitro and in vivo.

The invention is further described by the following examples, which are illustrative of the invention but do not limit the invention in any manner.

EXAMPLE 1

Construction of a Recombinant VV Having Integrated a Prodrug Converting Polypeptide Encoding Gene A) Construction of the Prototype AZT-Sensitive Virus vsuci2-L. Construction of Plasmids.

ptk-D4-suci. The tdk/tmk fusion gene was PCR-amplified from the plasmid pGT63-LacZ (Invivogen Inc, California) using the primers o-mut(tdk)-1,5'-GTG CTT GGG ACC ATG GCA GAG CTA TAT TTC-3' (SEQ ID NO: 1) and omut(tdk)-2 5'-CGG GCC GCG TCG GAA GCT TAG GCG TCC AAC TCC-3' (SEQ ID NO: 2) and placed under control of the vaccinia promoter P7.5. This expression cassette was cloned between sequences of the vaccinia tk-locus for homologous recombination together with the vaccinia D4R gene as a rescue marker under control of its natural promoter.

pDD4.4-suci2. The tdk/tmk fusion gene was excised from the plasmid pGT63-lacZ as a NcoI/HindIII fragment and inserted into NcoI/HindIII digested plasmid pDD4-P7.5, a derivative of pER Holzer et al., *Virol.* 249:160–166 (1998), which contains the P7.5 promoter followed by a multiple cloning site in the intergenic region between the vaccinia D4R and D5R genes. It is used for the construction of the virus v-suci2-L, which is based on the former vaccine strain Lister. The tk/tmk gene was inserted into an intergenic region (between ORFs D4R/D5R) that does not affect growth properties and virulence significantly. The virus does not contain further marker genes.

Construction of recombinant viruses. Infection, plasmid transfection and plaque purification for the generation of recombinant virus were performed essentially as described Holzer et al., 1998; supra.

v-suci2-L. The plasmid pDD4.4-suzi2 was transfected into CV1 cells previously infected with the defective parental virus dVV-L, which was constructed by deleting the D4R ORF (located between ORFs D3R and D5R) and substituted by a small insert of noncoding DNA in a Lister-based vaccinia virus. Plaques were purified in three passages in CV1 cells. During these plaque purifications, the recombinant v-suci2-L isolates were selected by their ability to grow normally, while the parental defective virus cannot propagate outside the complementing RK44 cell line. After three rounds of plaque purification, the isolates were grown to large scale, crude stocks were prepared. Crude stocks were titered in the absence of AZT and tested for inhibition in the presence of AZT (1.25 mg/ml) to verify the purity of the isolate. The plasmid pDD4.4-suzi2 and the smallpox vaccine strain Lister were used to construct the novel drug-sensitive vector, termed vsuci2-L, as schematically outlined in FIG. 2C.

vtk-suci2. Twenty micrograms of plasmid ptk-D4-suci were transfected into eVAC-1 infected CV-1 cells and viruses were obtained by dominant host range selection as described above. The replicating tk-negative virus vtk-Z and the defective virus eVAC-1 are described elsewhere. Holzer et al., *J. Virol.* 73: 4536–4542 (1999).

B) Inhibition of Plaque Formation in Cell Culture by AZT

Next, the minimal inhibiting prodrug dose using the two tk/tmk-positive viruses vtk-suci2 and vsuci2-L (the former is vaccinia tk-negative and the latter vaccinia tk-positive) and two control viruses, vtk-Z and wild-type vaccinia were studied. Although it is known that (tk-positive) wild-type vaccinia is not inhibited by AZT, the role of the endogenous tk-gene on the inhibitory dose of AZT was to be ascertained.

The four viruses were titered at different concentrations of AZT in CV-1 cells and also in the rabbit kidney cell line RK44.20 used for complementation of defective viruses (Table 1). Sixwell plates of cells were infected with 50 pfu/well of the indicated viruses and were incubated at increasing AZT concentrations. Plaques were visualized 3 days after infection by crystal violet staining. The tdk/tmk expressing viruses could be completely inhibited at AZT concentrations $\geq 0.25$ mg/ml in CV-1 cells. Viruses without the tk/tmk gene formed clearly visible plaques up to 1 mg/ml AZT. However, a gradual reduction in plaque size and number was observed, being detectable at 0.5 mg/ml of the prodrug. The AZT sensitivity of eVAC-1, a defective virus bearing no suicide gene, was also tested. Plaques were still detectable at 1 mg/ml of the drug although at a moderately reduced numbers. The toxic effect on CV-1 and RK44.20 cells was observed at AZT concentrations >1.5 mg/ml. The vaccinia tk-gene had no inhibiting effects on virus growth in the presence of AZT. Surprisingly, however, double tk-positive viruses were more sensitive to AZT inhibition (Table 1). As a conclusion, a concentration of 0.5 mg/ml AZT suppressed all types of suicide gene bearing viruses, without significant interference with recombinants that are lacking the suicide gene. The only exception is the virus vtk-suci2 grown in RK44.20 cells, which needed 0.75 mg/ml for full inhibition.

TABLE 1

Inhibition of VV recombinants by AZT.

| virus | genotype Suci | Vaccinia VVtk | Vaccinia strain | Cell line | % growth at AZT concentration (mg/ml) | | | | |
|---|---|---|---|---|---|---|---|---|---|
| | | | | | 0 | 0.25 | 0.5 | 0.75 | 1.0 |
| vsuci2-L | + | + | Lister | CV1 | 100 | -- | -- | -- | -- |
| VV Wt | − | + | Lister | CV1 | 100 | 100 | 100 | 100* | 80* |
| vtk-suci2 | + | − | WR | CV1 | 100 | --** | --** | -- | -- |
| vtk-Z | − | − | WR | CV1 | 100 | 100 | 90 | 30* | --** |
| vsuci2-L | + | + | Lister | 44.20 | 100 | --** | -- | -- | -- |
| VV Wt | − | + | Lister | 44.20 | 100 | 100 | 100 | 100 | 100* |
| vtk-suci2 | + | − | WR | 44.20 | 100 | 50 | 20* | --** | -- |
| vtk-Z | − | − | WR | 44.20 | 100 | 100 | 100* | 100* | 100* |
| evac-1 | − | + | WR | 44.20 | 100 | 100 | 100 | 100 | 100 |

*plaques 50% of normal size; **minute lesions detectable; --total inhibition.

D) Reversion rate of tdk/tmk positive vaccinia virus. High frequency of escape mutants (20–90% or more) are known to occur with classical vaccinia tk-negative selection, thereby requiring the use of an additional positive selection or screening marker. Usually, between 10–80% of tk-negative plaques are formed by recombinants, although the percentage may be significantly lower Chakrabarti et al. *Mol. Cell Biol.* 5: 3403–09 (1985).

The reversion rate of tdk/tmk expressing viruses therefore is of interest. In inhibition experiments, 10,000 pfu of drug-sensitive virus, plated under AZT onto two Roux bottles, did not result in visible escape mutants suggesting reversion rates <$1:10^4$ (<0.01%). Spiking experiments with 100 pfu wild-type virus per flask done in parallel showed that tk/tmk-negative virus can be detected in the presence of drug-sensitive virus under the chosen experimental conditions. Higher infectivites per cell of drug-sensitive virus did not permit the detection of spiked wild-type viruses. The experiment demonstrates the surprisingly superior performance of tk/tmk selection over the classical procedure.

EXAMPLE 2

A) Inhibition of plaque formation in cell culture by AZT. Plaque formation of the candidate virus is strongly inhibited by AZT on the standard cell line CV-1 (FIG. 2). Cells were grown to confluency, infected with the indicated amount of virus per well and incubated in the presence (upper row) or absence of AZT. After three days, cells were stained with crystal violet. At the highest dose of 10,000 pfu per well, all cells were lysed without AZT (first well lower row), while in the presence of AZT only minor lesions were detectable. The extent of inhibition was in a similar range in rabbit kidney cells. The therapeutic window of AZT concentrations was between 0.25 to 1 mg/ml. In this concentration range, the virus is strongly inhibited while host cells were not visibly affected.

Figure 3:
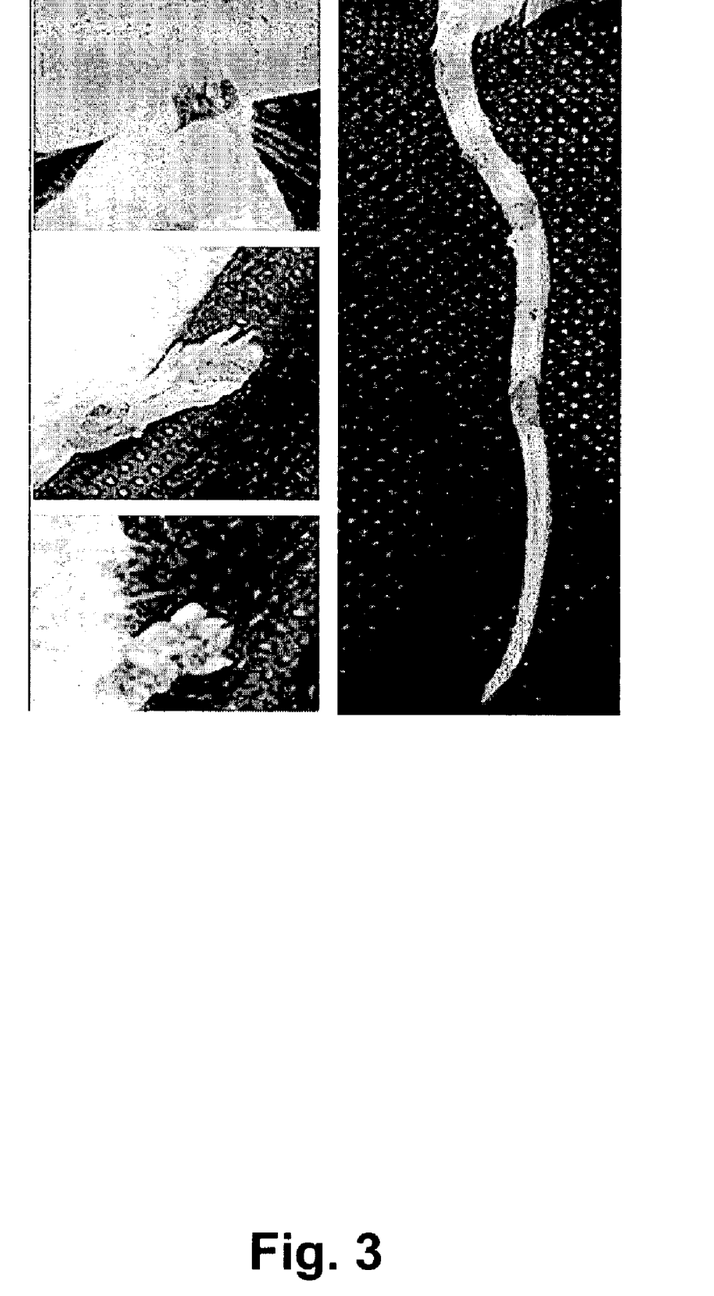

B) Inhibition of the AZT-sensitive vaccinia virus in SCID mice and treatment of generalized vaccinia. An important parameter to investigate is the in vivo inhibition of the prototype vaccine in animal models. Therefore, severely immunodeficient mice (Balb/c SCID mice) were challenged with a high dose ($10^8$ pfu, s.c.) of wt Lister virus and with AZT-sensitive virus. Groups of SCID mice were immunized subcutaneously with the indicated amounts of the different vaccinia strains or PBS. Mice were monitored for signs of progressive vaccinia virus disease for three months. Two independent experiments were performed. SCID mice developed generalized vaccinia within 2–4 weeks after injection of wild-type Lister virus, characterized by skin lesion in the tail, paw and mouth areas (FIG. 3). According to the treatment plan, early treatment beginning 4 hours after the challenge results in suppression of virus growth. Late treatment, 10–14 days after challenge, results in stabilization of the disease. No treatment results in death of the animals within 3–4 weeks. AZT was given orally in the drinking water in two different doses as indicated. The experiment is outlined in Table 2.

TABLE 2

Treatment of generalized vaccinia in SCID mice.

| group | dose s.c. | virus | treatment start AZT (mg/ml) | TIME (early, late) | symptoms |
|---|---|---|---|---|---|
| 1 | d8* | WT-L | 0.5 | E | gen VVD |
| 2 | d8 | WT-L | PBS | E | gen VVD |
| 3 | d8 | vsuci2-L | 0.5 | E | no disease |
| 4 | d8 | vsuci2-L | 1.0 | E | no disease |
| 5 | d8 | vsuci2-L | 0.5 | L | stab dis |
| 6 | d8 | vsuci2-L | 1.0 | L | stab dis |
| 7 | d8 | vsuci2-L | PBS | E | gen VVD |
| 8 | — | PBS | 0.5 | E | no disease | d8 means $1 \times 10^8$ pfu/animal; E means early treatment (4 hours after challenge); L means late treatment (10–14 days after challenge); gen VVD means generalized vaccinia disease; stab dis means stabilization of disease.

In vivo growth inhibition of AZT-sensitive virus, titration of virus in spleen, ovaries and brain. The presence or absence of the vaccinia tk-gene has a pronounced effect on the virulence of vaccinia virus. Tk-negative viruses were attenuated. Therefore, a detailed study to confirm that a novel tk-fusion gene does not affect significantly the virulence of the (double tk-positive) vaccine strain is desirable. Results reveal that due to somewhat reduced growth properties in cell culture usually seen with recombinant vaccinia viruses (compared to the Lister wild-type strain), the tk/tmk-positive virus has not gained virulence.

In vivo growth studies in SCID mice were performed. Mice were challenged with $10^8$ pfu of virus, and the time dependence of virus replication over 28 days in target organs such as spleen, brain and ovaries was determined (Table 3). Two animals per titer were sacrificed at days 0, 4, 8, 12, 16, 20, 24 and 28. At each time point, 2 mice per group (8 mice) were sacrificed, spleens, brain and ovaries collected for titration.

TABLE 3

In vivo growth curves of drug-sensitive vs wild-type virus.

| group | dose (sc) | virus | treatment AZT (mg/ml) | TIME | symptoms |
|---|---|---|---|---|---|
| 1 | d8 | WT-L | 0.5 | E | high titer in spleen/gen VVD |
| 2 | d8 | vsuci2-L | 0.5 | E | low titer in spleen/no disease |
| 3 | d8 | vsuci2-L | 0.5 | L | some titer in spleen/stab dis |
| 4 | d8 | vsuci2-L | PBS | E/PBS | high titer in spleen/gen VVD |

WT-L means wild-type Lister strain; vsuci2-L is a drug-sensitive vaccinia virus; E means early; L means late; gen VVD means generalized vaccinia disease; stab dis means stabilization of disease.

Both standard vaccine and drug-sensitive vaccine grow to similar titers without AZT, thereby showing equivalence in virulence of both viruses, which is required for efficient induction of neutralizing antibodies. In the presence of AZT, the sensitive virus was significantly inhibited. In case of late treatment, the virus titer declines in a dose dependent way confirming that it can be controlled by a standard antiviral drug. The data is set forth in Table 3 above.

EXAMPLE 3

Construction of a Candidate Smallpox Vaccine Based on the New York City Board of Health (NYCBH) Strain An AZT-sensitive vaccinia virus based on NYCBH strain is desirable because this strain is one of most successfully used smallpox vaccines during the era of smallpox eradication. The plasmid pDD4.4-suzi2-ZG is used to construct the virus v-AZTs-NYCBH strain by standard recombination procedures. All manipulations requiring virus growth are performed in a serum-free Vero cell line (VeroSF) approved for vaccine production, adapting the calf-lymph derived Dryvax vaccine to growth in the permanent cell line. See U.S. Pat. No. 6,146,873. Recombination, plaque purification and production is done in this cell line ensuring freedom from adventitious agents, in particular bovine viruses and BSE. This procedure ensures maximum product safety and excellent growth of candidate vaccine in the production cell line.

pDD4.4-suzi2-ZG. A 4.7 kb SnaBI/Not fragment containing a transient lacZ/gpt marker cassette (obtained from the vector pDW Holzer et al. 1999, supra) is inserted between the singular restriction sites SmaI and NotI downstream of the suicide gene in the plasmid pDD4.4-suzi2. The resulting plasmid is termed pDD4.4-suzi2-ZG. This plasmid directs the P7.5-tk/tmk gene cassette into the intergenic region D4/D5 and permits transient dominant selection with the gpt/lacZ procedure resulting in a recombinant virus free of additional selection markers.

Construction of the virus v-AZTs-NY. The plasmid pDD4.4-suzi2-ZG is transfected into VeroSF cells previously infected with the vaccinia virus (Dryvax, Wyeth Vaccines, obtained from Acambis, Inc.) according to standard procedures. Plaques are picked and selected for the gpt marker and screened for blue plaques. In two following rounds of plaque purification, isolates are grown without selective pressure and are screened for white plaques to obtain isolates that have deleted the instable selection marker cassette. The isolates are then grown to large scale. Virus stocks are titered in the absence of AZT and tested for inhibition in the presence of AZT to verify the purity of the isolate.

EXAMPLE 4

Figure 4:
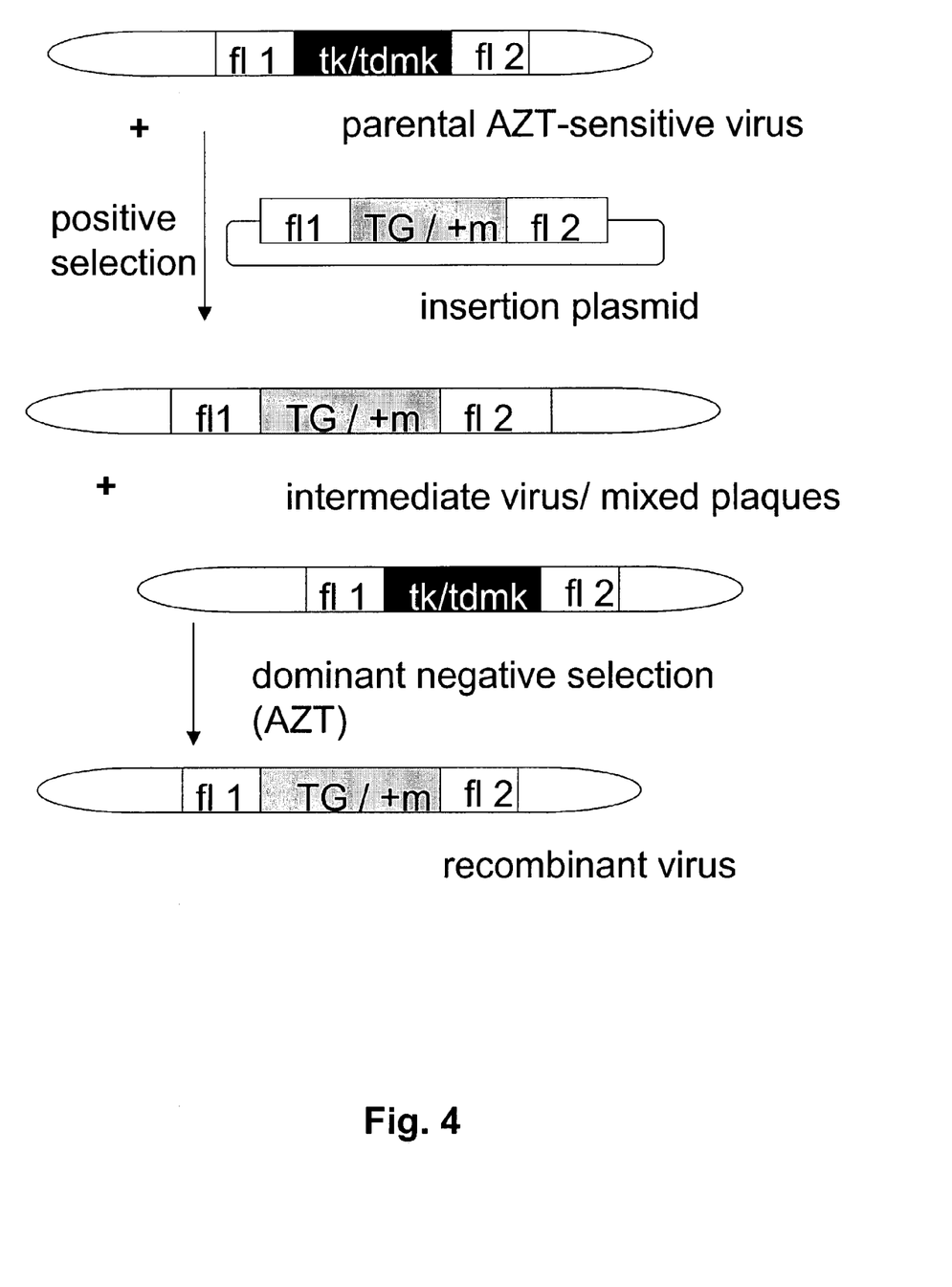
Figure 5:
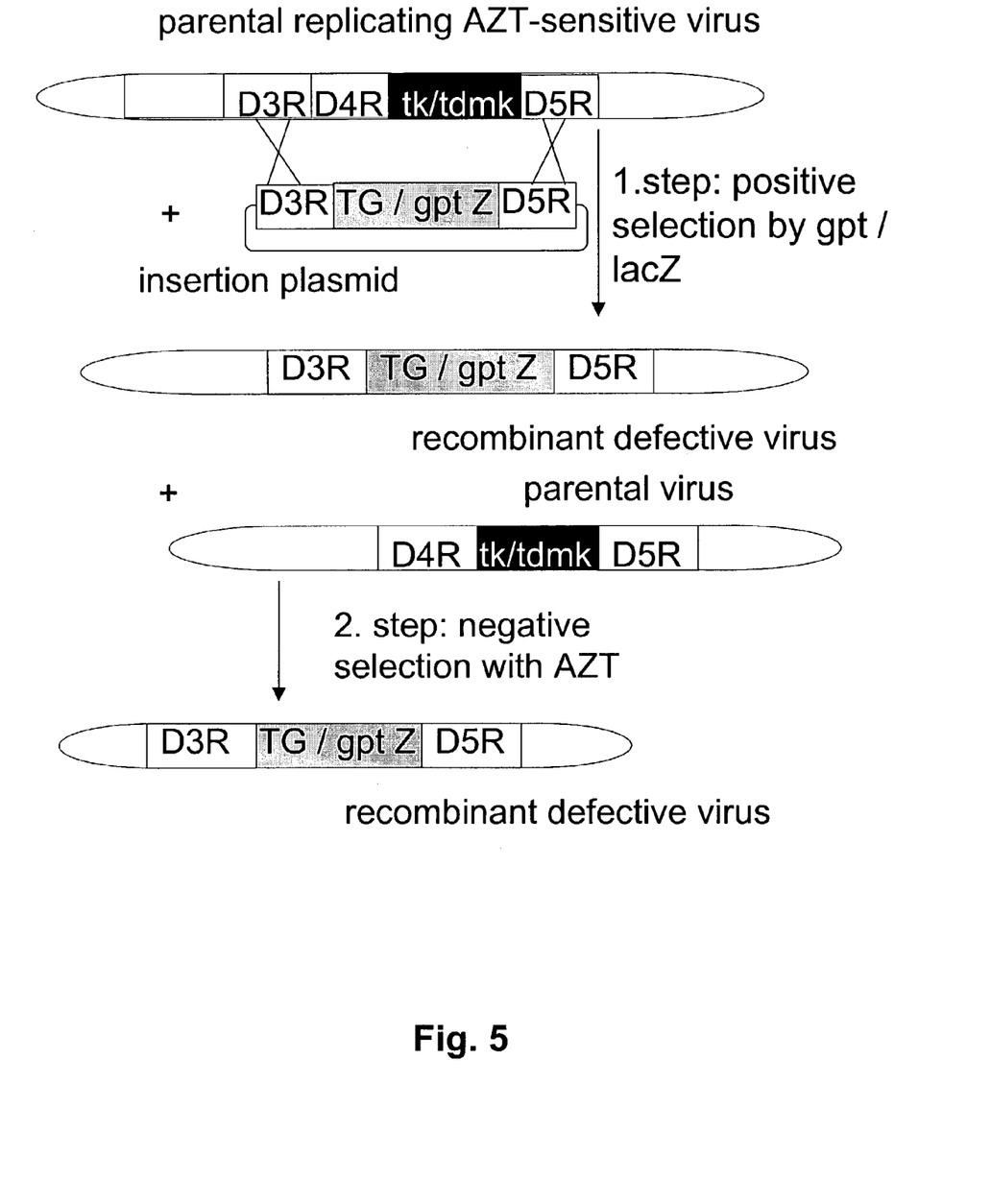

The new recombinant vaccinia comprising a gene encoding a prodrug converting polypeptide also allows for a new selection method, an efficient negative selection protocol could be established even for vaccinia recombinants that are otherwise difficult to isolate, and where classical vaccinia tk selection is not possible. The novel *E. coli* tk/tmk marker provides stringent selection and shows a low frequency of escape mutants, allowing for rapid isolation of recombinants starting with a tk/tmk-positive parental virus. A schematic drawing of the selection procedure and the construction is presented in FIGS. 4 and 5.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

What is claimed is:

1. A method of vaccinating a subject against smallpox, wherein the method comprises
administering to the subject in need of smallpox vaccination a recombinant vaccinia virus having integrated into its viral genome an exogenous sequence encoding a prodrug converting polypeptide under transcriptional control of a poxvirus regulatory region, wherein said prodrug converting polypeptide can convert a prodrug into a drug that inhibits vaccinia virus replication.

2. The method according to claim 1, wherein the vaccinia virus is a smallpox vaccine strain selected from the group of strains consisting of Lister/Elstree, New York City Board of Health, Temple of Heaven and LC16 m2.

3. The method according to claim 1, wherein the exogenous sequence is integrated into a non-essential region of the viral genome.

4. The method according to claim 1, wherein the non-essential region is an intergenic region.

5. The method according to claim 1, wherein the prodrug converting polypeptide is a thymidine kinase from herpes simplex virus or cytomegalovirus.

6. The method according to claim 1, wherein said prodrug converting polypeptide is a fusion protein.

7. The method according to claim 6, wherein the fusion protein is *E.coli* thymidine kinase/thymidylate kinase (tk/tmk).

8. The method according to claim 1, wherein the prodrug is a nucleoside analog.

9. The method according to claim 1, wherein the prodrug is selected from the group consisting of 3'azido-2',3'-dideoxythymidine (AZT), gancyclovir (GCV) and acyclovir (ACV).

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 1
gtccttgcca ccatggcaca gctatatttc                30

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 2
cgggccgcgt cggaagctta cgcgtccaac tcc             33

10. A method to treat a vaccinated subject showing signs of vaccination-induced disease after needed vaccination with a smallpox vaccine comprising recombinant vaccinia virus having integrated into its viral genome an exogenous sequence encoding a prodrug converting polypeptide under transcriptional control of a poxvirus regulatory region, wherein the method comprises the step of
   administering to the vaccinated subject a prodrug in an effective dose for a time sufficient to at least reduce the titer of recombinant vaccinia virus, wherein the prodrug is converted by the prodrug converting polypeptide to a drug that inhibits viral replication.

11. The method according to claim 10, wherein the prodrug is selected from the group consisting of 3'azido-2', 3'-dideoxythymidine (AZT), gancyclovir (GCV) and acyclovir (ACV).

12. The method according to claim 10, wherein the inhibition of replication of vaccinia is monitored by determination of viral load of the organism.

13. The method according to claim 10, whereby the prodrug is given orally, intravenously or topically.

14. The method of claim 10, further comprising administering an anti-vaccinia immune globulin to the vaccinated subject.

* * * * *